(12) United States Patent
Hannemann et al.

(10) Patent No.: US 9,664,801 B2
(45) Date of Patent: May 30, 2017

(54) METHOD AND DEVICE FOR DETERMINING THE X-RAY RADIATION ATTENUATION CAUSED BY THE OBJECT TO BE EXAMINED

(71) Applicant: Siemens Aktiengesellschaft, Munich (DE)

(72) Inventors: Thilo Hannemann, Erlangen (DE); Mario Reinwand, Breitbrunn (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 187 days.

(21) Appl. No.: 14/420,752

(22) PCT Filed: Jul. 18, 2013

(86) PCT No.: PCT/EP2013/065200
§ 371 (c)(1),
(2) Date: Feb. 10, 2015

(87) PCT Pub. No.: WO2014/044430
PCT Pub. Date: Mar. 27, 2014

(65) Prior Publication Data
US 2015/0219774 A1 Aug. 6, 2015

(30) Foreign Application Priority Data

Sep. 24, 2012 (DE) .................. 10 2012 217 177
Jan. 14, 2013 (DE) .................. 10 2013 200 400

(51) Int. Cl.
*A61B 6/00* (2006.01)
*G01T 1/36* (2006.01)
(Continued)

(52) U.S. Cl.
CPC .............. *G01T 1/36* (2013.01); *A61B 6/032* (2013.01); *A61B 6/4014* (2013.01);
(Continued)

(58) Field of Classification Search
CPC G01T 1/36; G01T 1/17; A61B 6/4241; A61B 6/032; A61B 6/4014; A61B 6/5258; A61B 6/482; A61B 6/0457; A61B 6/5205
(Continued)

(56) References Cited

U.S. PATENT DOCUMENTS

| 4,458,358 A | 7/1984 | Klausz |
| 5,148,455 A | 9/1992 | Stein |

(Continued)

FOREIGN PATENT DOCUMENTS

| CN | 1954779 A | 5/2007 |
| CN | 101416073 A | 4/2009 |

(Continued)

OTHER PUBLICATIONS

B. Gonzales,"Full-Spectrum CT Reconstruction Using a Weighted Least Squares Algorithm With an Energy-Axis Penalty", IEEE Transactions on Medical Imaging, IEEE Service Center, Piscataway, NJ, vol. 30, No. 2, Feb. 1, 2011, 11 pgs.

(Continued)

*Primary Examiner* — Courtney Thomas
(74) *Attorney, Agent, or Firm* — Harness, Dickey & Pierce, P.L.C.

(57) ABSTRACT

An embodiment of the invention relates to the use of the spectral composition of X-ray radiation in addition to the intensity thereof in order to determine the attenuation caused by an object. Another aspect of an embodiment of the invention is a device, particularly a radiation monitor for an (Continued)

X-ray or CT system, which is suitable for performing the aforementioned procedure according to an embodiment of the invention.

26 Claims, 2 Drawing Sheets

(51) Int. Cl.
  *A61B 6/03* (2006.01)
  *G01T 1/17* (2006.01)
  *A61B 6/04* (2006.01)
(52) U.S. Cl.
  CPC ............ *A61B 6/4241* (2013.01); *A61B 6/482* (2013.01); *A61B 6/5258* (2013.01); *G01T 1/17* (2013.01); *A61B 6/0457* (2013.01); *A61B 6/5205* (2013.01)
(58) Field of Classification Search
  USPC .................................................. 378/4–20, 62
  See application file for complete search history.

(56) References Cited

U.S. PATENT DOCUMENTS

| | | | |
|---|---|---|---|
| 6,748,043 B1 | 6/2004 | Dobbs | |
| 7,139,362 B2 | 11/2006 | Heismann et al. | |
| 7,769,132 B1* | 8/2010 | Hurd .................... | A61B 5/0033 378/57 |
| 2004/0028181 A1* | 2/2004 | Charles, Jr. et al. .. | A61B 6/032 378/92 |
| 2007/0081622 A1 | 4/2007 | Bruder et al. | |
| 2008/0279328 A1 | 11/2008 | Zeitler et al. | |
| 2010/0008558 A1 | 1/2010 | Baeumer et al. | |
| 2010/0061504 A1 | 3/2010 | Proksa | |
| 2010/0232669 A1 | 9/2010 | Ziegler et al. | |
| 2011/0096892 A1* | 4/2011 | Forthmann ............ | A61B 6/032 378/5 |
| 2011/0309251 A1 | 12/2011 | Fenchel et al. | |
| 2012/0093282 A1 | 4/2012 | Kappler | |
| 2014/0072098 A1* | 3/2014 | Kappler ................. | A61B 6/032 378/19 |

FOREIGN PATENT DOCUMENTS

| | | |
|---|---|---|
| CN | 101557762 A | 10/2009 |
| CN | 102076283 A | 5/2011 |
| CN | 102293662 A | 12/2011 |
| CN | 102440801 A | 5/2012 |
| DE | 28 00 761 A1 | 7/1979 |
| DE | 10212638 A1 | 10/2003 |
| EP | 0608237 A1 | 8/1994 |
| WO | WO-2007/057841 A2 | 5/2007 |
| WO | WO-2008059425 A2 | 5/2008 |
| WO | WO-2008/068674 A2 | 6/2008 |
| WO | WO-2008059425 A3 | 7/2008 |

OTHER PUBLICATIONS

S. Feuerlein, "Multienergy Photon-counting K-edge Imaging: Potential for Improved Luminal Depiction in Vascular Imaging", Radiology, vol. 249, No. 3, Oct. 10, 2008, 7pgs.

E. Roessl, "K-edge imaging in x-ray computed tomography using multi-bin photon counting detectors; K-edge imaging based on photon counting detectors", Physics in Medicine and Biology, Institute of Physics Publishing, Bristol GB, vol. 52, No. 15, Aug. 7, 2007, 18 pgs.

International Search Report PCT/ISA/210 for International Application No. PCT/EP2013/065200 dated Jul. 18, 2013.

International Preliminary Report on Patentability for International Application No. PCT/EP2013/065200 mailed Sep. 24, 2012.

B. Gonzales,"Full-Spectrum CT Reconstruction Using a Weighted Least Squares Algorithm With an Energy-Axis Penalty", *Ieee Transactions on Medical Imaging*, vol. 30, No. 2, Feb. 1, 2011, p. 173-183.

S. Feuerlein, "Multienergy Photon-counting K-edge Imaging: Potential for improved Luminal Depiction in Vascular Imaging", *Radiology*, vol. 249, No. 3, Dec. 2008, p. 1010-1016.

E. Roessl, "K-edge imaging in x-ray computed tomography using multi-bin photon counting detectors," *Physics in Medicine and Biology*, Institute of Physics Publishing, Bristol GB, vol. 52, 2007, p. 4679-4696.

German Report on Examination dated Sep. 20, 2013 for corresponding DE Application No. 10 2013 200 400.1.

Biao Cai: "Simulation of Computed Tomography Reconstruction Algorithm Based on Consecutive X-ray Spectrum"; pp. 257-260; vol. 28; No. 4; 2011.

Office Action for Chinese Application No. 201380045976.4 issued on May 16, 2016 and English translation thereof.

Chinese Office Action for Chinese Application No. 201380045978.4 issued on Jan. 20, 2017.

* cited by examiner

METHOD AND DEVICE FOR DETERMINING THE X-RAY RADIATION ATTENUATION CAUSED BY THE OBJECT TO BE EXAMINED

PRIORITY STATEMENT

This application is the national phase under 35 U.S.C. §371 of PCT International Application No. PCT/EP2013/065200 which has an International filing date of Jul. 18, 2013, which designated the United States of America, and which claims priority to German patent application numbers DE 102012217177.0 filed Sep. 24, 2012 and DE 102013200400.1 filed Jan. 14, 2013, the entire contents of each of which are hereby incorporated herein by reference.

FIELD

At least one embodiment of the invention generally relates to methods for determining the attenuation of the x-ray radiation caused by the object to be examined. Furthermore, at least one embodiment of the invention generally relates to a device, in particular a radiation monitor for an x-ray or CT (CT=computed tomography) system, which device, in particular, is suitable for carrying out the method.

BACKGROUND

The x-ray technology used in CT imaging is an important technology in medical imaging.

FIG. 1 shows, in an example manner, the setup of a modern so-called dual source CT system; however, embodiments of the invention are not restricted thereto.

Such a CT system 1 comprises a first x-ray tube or x-ray radiation source 2 with a detector 3 opposite thereto and a second x-ray tube 4 with a further detector 5 opposite thereto, wherein x-ray source and detector are arranged in such a way that a patient 7 to be penetrated by x-ray radiation can be placed between the two. The two x-ray radiation source and detector systems 2, 3 and 4, 5 are arranged in a gantry housing 6 on a gantry, which rotates about a system axis 9 and is not visibly depicted here. The patient 7 is situated on a longitudinally displaceable patient couch 8, which is pushed continuously or in a step-by-step manner through an opening in the gantry housing 6 for the purposes of scanning the patient 7 during the rotation of the x-ray radiation source and detector systems. As a result of this, the patient 7 is scanned in a helical or multiple circular manner, wherein x-ray radiation generated by the x-ray source penetrates the patient and is registered after the penetration thereof at a detector.

A control and computer unit 10 having computer programs and program modules Prgx, which are loaded and worked through as required during operation, in the memory 11 thereof serves to control the CT system 1. The control itself and the readout of detector output data is brought about by means of the control and data line 12, which connects the control and computer unit 10 with the gantry housing 6.

CT technology and, more generally, medical x-ray diagnostics ultimately are based on the fact that the object to be imaged, e.g. a patient 7, is penetrated by x-ray beams and that, in the process, the x-ray radiation is locally attenuated in terms of its intensity. Measuring the attenuation of the x-ray radiation allows conclusions to be drawn in respect of the object to be imaged. The attenuation to be measured emerges by way of the radiation intensity which the x-ray detector registers when the object is present compared to the radiation intensity that would be registered without the presence of the object.

If the x-ray radiation source is not stable in time and if it emits x-ray radiation that varies in terms of the intensity thereof, then the detector would detect different radiation intensities over time, even without the presence of an object. It is possible to measure the radiation intensity emitted by the x-ray radiation source by means of a so-called radiation monitor. Then, this measured value can be used in the evaluation of the detector signals.

A radiation monitor for x-ray radiation, used for this purpose, is a device including at least one sensor that can measure the intensity of x-ray radiation. The sensor (which is also referred to as a radiation monitor element) is introduced into the region irradiated by the x-ray radiation. Depending on the measured radiation intensity, the radiation monitor emits a signal which, for example, can be indicated, used for controlling the radiation generation process and used in the processing of the signal data from the detector. Here, a radiation monitor is generally configured in such a way that it is not situated in the region of the radiation field provided for determining the attenuation through the object, but rather situated in a different region of the radiation field which, however, is characteristic for the whole radiation field in terms of the properties registered by the radiation monitor.

SUMMARY

An embodiment of the invention improves a determination of an attenuation of the x-ray radiation caused by the object to be examined.

A method and a device are disclosed in accordance with the independent patent claims. Advantageous embodiments of the invention are the subject matter of the dependent patent claims or can be gathered from the following description and the example embodiments.

One aspect of an embodiment of the invention is that of determining an attenuation of x-ray radiation as a result of the latter penetrating through an object to be examined, wherein an intensity of the x-ray radiation respectively before and after penetrating the object is established for the purposes of determining the attenuation. The spectral composition of the x-ray radiation is determined prior to the latter penetrating the object and said spectral composition is taken into account when determining the attenuation.

Expressed differently, the spectral distribution of the intensity of the x-ray radiation is determined or measured near the x-ray radiation source or on the side of the object facing the x-ray source. Establishing the spectral composition can mean that the composition is established over the whole x-ray spectrum. However, this is not necessary. Establishing the spectral composition can also mean that the intensity of the x-ray radiation is established separately in at least two different energy ranges.

As a result, inaccuracies, which can have an effect on image processing in post-processing and would otherwise occur due to the time variation of the x-ray spectrum, can be corrected when determining the attenuation of the intensity of the x-ray radiation.

Here, an embodiment of the invention is based on the discovery that not only the intensity but also the spectral composition of the x-ray radiation can be important for determining the attenuation of the x-ray radiation. By way of example, the spectral composition of the x-ray radiation becomes important if use is made of a spectrally resolving detector.

What was identified here is that correcting intensity variations, as described above, may sometimes be insufficient for achieving a satisfactory result.

This is because the x-ray radiation emitted by the x-ray source of a medical instrument has a spectral composition comprising a multiplicity of wavelengths—or correlating therewith—photon energy levels. The maximum photon energy level occurring in the spectral composition is equal to the accelerating voltage of the tube, i.e. the voltage applied between cathode and anode.

Now, not only can the intensity of the x-ray radiation vary overall, but the spectral composition may also lack the desired constancy in time. There can be many different reasons for this: by way of example, a change in the spectral composition occurs, in particular, at the start and end of the radiation generation. As a result of regulating the x-ray radiation source or emitter, there may also be variations of the accelerating voltage required for generating the radiation and, as a result, there may be a variability of the emitted x-ray spectrum. Furthermore, the surface structure of the focal track of the x-ray emitter may also lead to a change in the x-ray spectrum.

What was identified here is that, in addition to the intensity, it is advantageous also to use the spectral composition of the x-ray radiation emitted by the x-ray source for the purposes of determining the attenuation.

In principle, it is also possible to keep the accelerating voltage of the x-ray emitter as stable as possible during operation and not to evaluate the radiation detected at the beginning and in the end phase of the radiation where the spectral composition is changeable. However, a disadvantage of this solution lies in the technical complexity for stabilizing the accelerating voltage required for the radiation generation and the dose loss as a result of discarding the x-ray radiation emitted at the start and at the end of the radiation. Although the dose loss could be reduced by a mechanical closure or shutter, an additional component would also be required in this case.

However, a satisfactory result can also be achieved by the method according to an embodiment of the invention when the spectral composition of the x-ray radiation is not constant or when it varies. This is because the spectral composition of the x-ray radiation is determined prior to the penetration through the object and taken into account when determining the attenuation by evaluating the detector data. This can be used to determine changes in the spectral composition of the x-ray radiation. By way of example, instabilities in the accelerating voltage in the start and end phase of the radiation generation can be identified and compensated for.

Moreover, the spectral composition can be logged in a time resolved manner, that is to say at least two different times or, better, continuously in order to put the measurement data, which are likewise recorded in a time resolved manner, i.e. the intensity of the x-ray radiation, after the penetration of the object into a corresponding relationship.

Taking into account the spectral composition when determining the attenuation can also be implemented by virtue of a further spectral composition of the x-ray radiation also being determined after the penetration of the x-ray radiation through the object, for example by means of a spectrally resolving detector, and a comparison with the corresponding portions of the spectral composition of the x-ray radiation determined prior to the penetration being included when determining the attenuation. The spectral composition of the x-ray radiation can be decomposed into energy ranges corresponding to the portions.

Here, there are a number of options for determining the spectral composition of the x-ray radiation and for subsequently using the latter when determining the attenuation of the detector data.

The spectral composition of the x-ray radiation prior to penetrating an object to be examined can be determined by a radiation monitor. Here, the radiation monitor can be embodied e.g. in such a way that it logs the spectral composition of the x-ray radiation in a spectrally resolved manner by virtue of logging or registering the x-ray radiation divided into different energy ranges (that is to say into different "energy bins").

Here, the energy ranges of the radiation monitor can be configured in such a way that these correspond to the energy ranges of the detector, provided that a spectrally resolving detector is used. As a result, the data from the detector can easily be corrected and compared to the data of the radiation monitor.

Thus, for example, one embodiment for determining the attenuation can provide for the ratio between the intensity of the x-ray radiation established by the detector after the penetration and the intensity of the x-ray radiation established by the radiation monitor prior to the penetration to be calculated for the respectively same energy range. This is included in the determination of the attenuation. It is very advantageous for this process if the energy ranges of the radiation monitor and of the spectrally resolving detector already correspond.

Alternatively, the radiation monitor can be configured in such a way that it logs the whole x-ray spectrum in a spectrally resolved manner. If the whole spectrum is known, it is also possible to take the beam hardening, i.e. the influence of the object on the spectrum, registered by the detector, into account. This leads to an even more accurate correction of the spectral variations of the x-ray source.

In order to establish the whole x-ray spectrum, it may already be sufficient to merely detect certain energy ranges by the radiation monitor. Then, conclusions about the whole x-ray spectrum can be drawn from the measurement data. Here, the whole spectrum is back-calculated from the measured radiation intensities of at least two energy ranges. It is therefore possible to draw conclusions about the whole spectral composition of the x-ray radiation from merely specific, suitable energy ranges because the spectrum of the x-ray radiation depends substantially only on the accelerating voltage and it is therefore possible to draw conclusions about the accelerating voltage, and thereby about the whole spectrum, from the relative signal of at least two energy ranges.

The spectral composition of the x-ray radiation prior to penetration through the object can, in one alternative embodiment of the invention, also be determined by virtue of measuring the accelerating voltage of the x-ray source in a time resolved manner, i.e. at time intervals within a period of time, and deriving the spectral composition of the x-ray radiation prior to the penetration through the object from the acceleration voltage. In particular, the time resolution is such that the effectively emitted spectrum can be determined within one integration time of the detector. The spectrum established in this manner can then for example in turn be transformed into reference values for determining the attenuation of the object.

A further aspect of at least one embodiment of the invention provides for a device, in particular a radiation monitor for an x-ray machine or CT system, including means that are suitable for carrying out the method described herein. Here, the x-ray machine comprises at least one x-ray source and at least one x-ray detector for the imaging examination of an object arranged between x-ray source and x-ray detector.

A development of at least one embodiment of the invention provides for devices to be present for establishing an intensity of the x-ray radiation emitted by the x-ray source and at least one device for determining a spectral composition of the x-ray radiation prior to the penetration thereof through the object to be examined. Furthermore, there are devices present for providing the established intensity and the determined spectral composition. These devices render it possible to use the established intensity and the determined spectral composition for determining the attenuation of the x-ray radiation after the penetration thereof through the object to be examined, for example in a post-processing method, in which an image of the object to be examined is generated from the recorded x-ray detector data.

The devices for determining the spectral composition of the x-ray radiation are arranged in the vicinity of the at least one x-ray source and/or can be integrated into the at least one x-ray source. In the case of a plurality of x-ray sources, these devices can be arranged at, or integrated in, each x-ray source or only at individual x-ray sources.

A development of at least one embodiment of the invention provides for at least one device for accepting the established intensity and the determined spectral composition and means for determining the attenuation of the x-ray radiation after the penetration thereof through the object, wherein the established intensity and the spectral composition of the x-ray radiation are usable for determining the attenuation.

A development of the device according to at least one embodiment of the invention provides for the latter to comprise at least two radiation monitor elements for each x-ray source. Here, the x-ray monitor elements are configured in such a way that they have different spectral sensitivity in respect of the spectral composition of the x-ray radiation that can be logged thereby. As a result, the spectral composition of the radiation can be established.

By way of example, use can be made of radiation monitor elements which are already present in any case in a computed tomography system. A CT machine typically includes e.g. one radiation monitor which comprises two position-resolving radiation monitor elements: a so-called Z-monitor (which is arranged axially in relation to the rotational movement of the gantry) and a so-called Phi-monitor (which is arranged in the direction of the rotational movement of the gantry). By way of example, these two radiation monitor elements render it possible to determine the location of the focal point of the x-ray radiation on the anode. At the same time, they can measure the intensity of the x-ray radiation and detect possible variations in the x-ray radiation connected therewith. If the two radiation monitor elements have a different spectral sensitivity, it is moreover possible to deduce the spectral composition of the x-ray radiation.

So that the radiation monitor elements may respectively have a different spectral sensitivity, a filter element may be applied to at least one of these radiation monitor elements.

Alternatively or additionally, the radiation monitor elements may include different converter materials or these converter materials may have different dimensions, e.g. thicknesses. It is also possible to obtain a different spectral sensitivity hereby.

A development of at least one embodiment of the invention provides for the device to be able to be embodied in the form of a direct conversion detector. This detector is able to distinguish between a plurality of energy ranges. This embodiment is expediently used if the x-ray detector is also based on this technology. Then, in particular, the x-ray detector and the direct conversion detector of the device have the same energy thresholds for the subdivision into the different energy ranges such that the measurement data from the device and from the x-ray detector directly correspond to one another. The post-processing or the correction of the x-ray detector data during the image reconstruction becomes simpler as a result thereof.

A development of at least one embodiment of the invention provides for the device to be able to be embodied in the form of a multi-layer detector, wherein the spectral sensitivity is realized with the aid of the various layers.

A development of at least one embodiment of the invention provides for the device to be able to be embodied in the form of a detector which includes a sensitive layer for converting photons into an electrical signal. By way of example, such a detector is known from the patent application WO2008/059425. Such a detector is advantageous in that it is particularly suitable for measuring photons.

BRIEF DESCRIPTION OF THE DRAWINGS

The details and developments of the device according to the invention are explained in more detail in the following example embodiments.

Further advantages, details and developments of the invention emerge from the following description of example embodiments in conjunction with the drawings. In the drawing.

DETAILED DESCRIPTION OF THE EXAMPLE EMBODIMENTS

Figure 2:
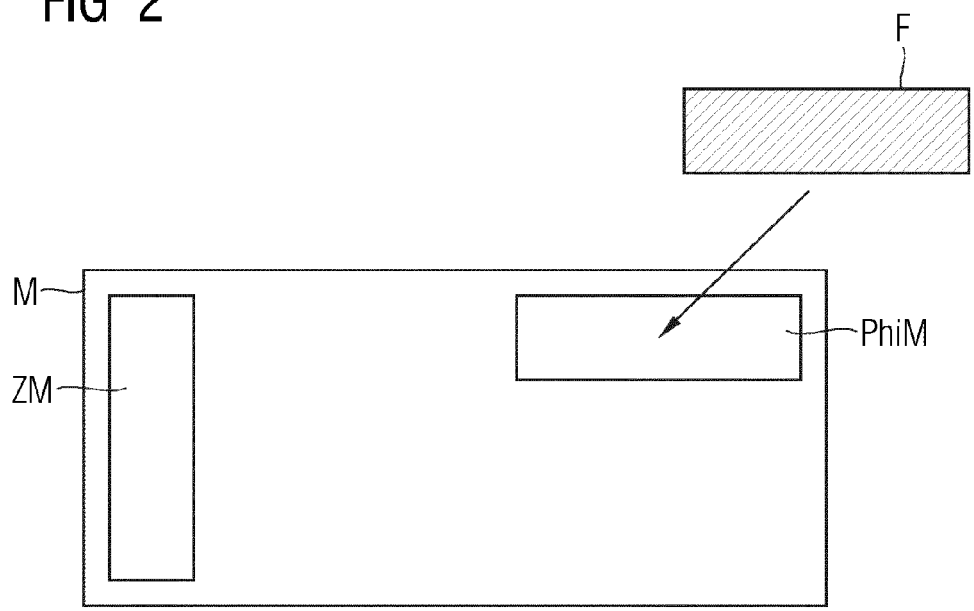

In accordance with FIG. 2, a radiation monitor M is embodied and arranged in the CT system 1 in such a way that the spectrum of the x-ray radiation can be determined with the aid thereof.

Figure 1:
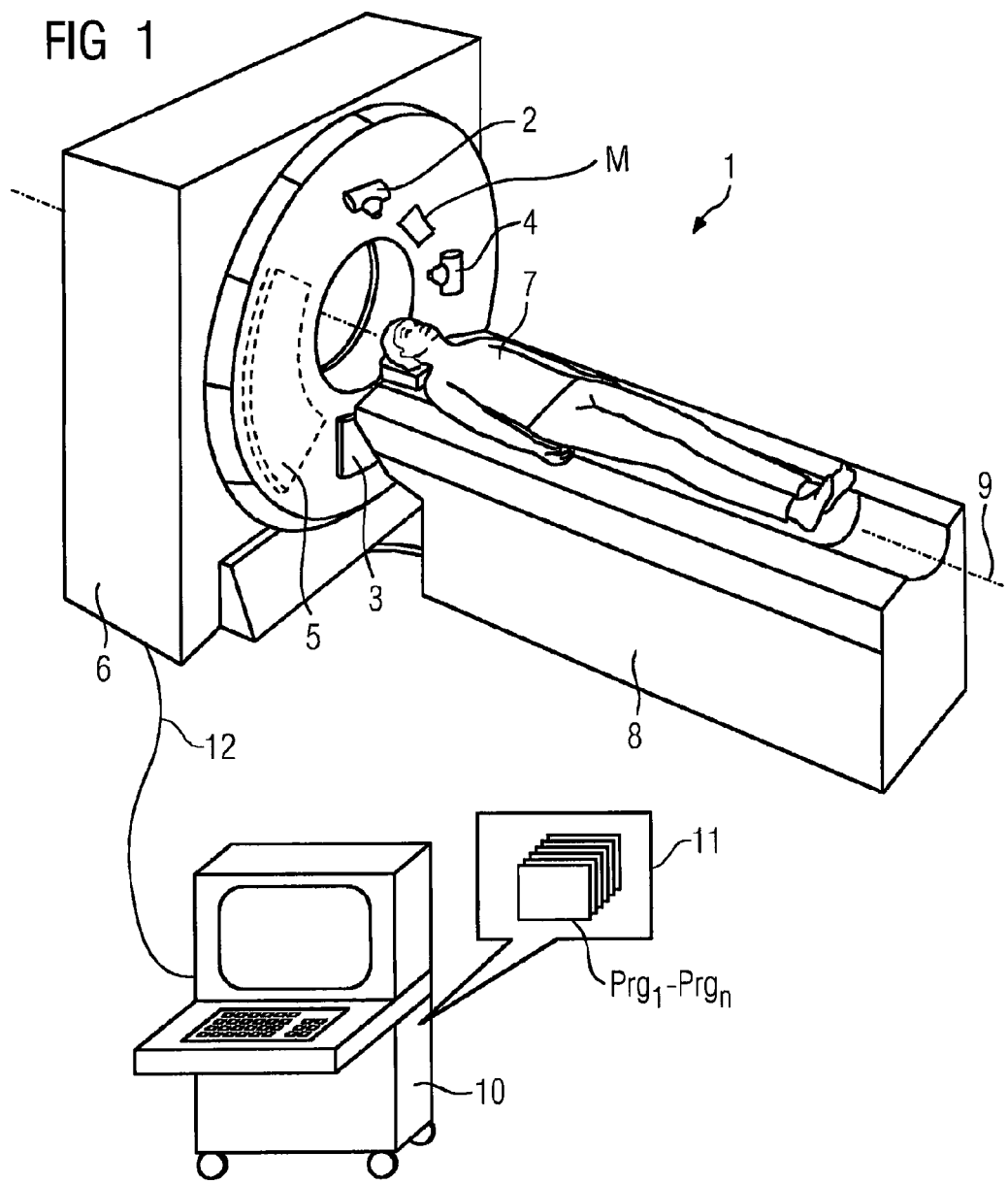
FIG. 1 shows the CT system mentioned at the outset and
FIG. 2 shows a radiation monitor in a CT system.

The radiation monitor M not depicted in FIG. 1 is preferably arranged in the vicinity of one x-ray radiation source or, in the case of a plurality of x-ray sources, in the vicinity of the x-ray radiation sources. However, in principle, it is feasible to also introduce the radiation monitor at any position in the radiation field. Here, a preferred position for the radiation monitor is the region of the so-called emitter shutter, i.e. the shutter which limits the radiation field of the x-ray emitter directly at the x-ray tube to the angular range of the radiation which is used for radiating through the object. Here, the radiation monitor is preferably arranged in such a way that it is arranged directly next to the shutter opening which predetermines the angular range of the radiation provided for radiating through the object. On the one hand, the used radiation is thereby not adversely affected by the radiation monitor. On the other hand, the radiation monitor logs part of the radiation which is spatially in the vicinity of the used radiation and therefore reproduces the properties of the used radiation in a representative manner.

Attenuation of the x-ray radiation caused by the object to be examined is determined by establishing the intensity of the x-ray radiation, respectively before and after penetration through the object. In addition to the intensity, the spectral composition of the x-ray radiation is also used for determining the attenuation. The latter can be logged prior to the penetration through the object with the aid of the radiation monitor.

Here, it is advantageous for the influence of a time variable spectrum of the x-ray radiation to be taken into account when determining the attenuation of the x-ray radiation caused by the object to be examined. In particular, such an embodiment is expedient if a spectrally resolving x-ray detector is used for recording the x-ray data for the image reconstruction.

When determining the attenuation, it is expedient to determine a further spectral composition of the x-ray radiation after the penetration through the object and to carry out a comparison with the corresponding portions of the spectral composition of the x-ray radiation determined prior to the penetration.

In the example embodiment described here, the radiation monitor M in a CT system is also used for determining the intensity of the x-ray radiation and for determining the focal point of the x-ray radiation on the anode of the x-ray tube.

To this end, the radiation monitor M includes at least two position resolving radiation monitor elements: the Z-monitor ZM (axially to the rotational movement of the gantry) and the Phi monitor PhiM (in the direction of the rotational movement of the gantry). The two radiation monitor elements ZM, PhiM are operated in such a way that they record both a position-dependent signal and an integrated signal, which maps the whole radiation intensity incident on the respective radiation monitor element, as a result of the measurement of the x-ray radiation registered by the radiation monitor elements. The two signals can be evaluated in the aforementioned control and computer unit 10.

A filter element F can be applied to at least one of these two radiation monitor elements such that the two radiation monitor elements have different spectral sensitivities. The spectrum of the x-ray radiation can be determined from the relative signal between the signals of the two monitors under the assumption that the spectral differences over time are caused by a change in the accelerating voltage.

Conventionally, the radiation monitor elements are made from an x-ray converter material (e.g. GOS=gadolinium oxysulfide) applied to an optical position-sensitive diode. Therefore, it is feasible not to change the spectral sensitivity with a filter but to modify said sensitivity by selecting different converter materials or different dimensions or thicknesses of the converter materials for the two radiation monitor elements.

The information relating to the spectral composition or the x-ray spectrum of the x-ray radiation can be established in various ways:

Firstly, the radiation monitor is configured in such a way that it can also establish the spectral composition of the x-ray radiation. Typically, a spectrally resolving detector registers the x-ray radiation of various energy ranges, wherein each energy range corresponds to a range of the x-ray spectrum. The radiation monitor can therefore record the x-ray spectrum in appropriate energy ranges, which are also referred to colloquially as "energy bins", in a "decomposed" manner.

If the x-ray detector likewise logs the x-ray radiation in a spectrally resolved manner with the same subdivision of the energy ranges in an analogous manner, the signals from the radiation monitor and detector can then e.g. be directly related to one another and a relative signal can be calculated therefrom.

A spectrally resolving detector generally has the unwanted property that it has a restricted spectral resolution, i.e. that the intensities registered in the "energy bins" do not exactly correspond to the energies of the registered photons. Additionally, systematic effects may also occur, e.g. the k-escape in the case of semiconductor detectors, and these then falsify the registered spectrum in relation to the actual spectrum. Said effect can be corrected by a computation if the detector properties are known. If the detector and the radiation monitor have the same falsification of the spectrum within the scope of this invention, such a computational correction is unnecessary if the energy ranges related to one another are falsified to the same extent.

A suitable selection of the "energy bins" of the radiation monitor also renders it possible to determine the whole x-ray spectrum of the x-ray radiation source from knowledge of the signal from at least two energy bins. This is because the x-ray spectrum depends primarily on the accelerating voltage. The accelerating voltage, and hence the whole x-ray spectrum, can be deduced from the relative signal of at least two energy bins.

Therefore, this also provides the option of dispensing with a spectrally resolving radiation monitor and instead measuring the accelerating voltage of the x-ray source in a time resolved manner or in a plurality of time intervals within a period of time and determining therefrom the emitted spectrum within the period of time, e.g. the start and end phase of the radiation generation. From this, variations or changes in the spectral composition can be derived and these can in turn be included in the determination of the attenuation of the x-ray radiation after penetration through the object.

It is likewise feasible to use this method in addition to a spectrally resolving radiation monitor in order, for example, to obtain a higher time resolution.

If the spectrum of the x-ray source is known, it is also possible to take into account the influence of the object itself on the spectrum registered by the detector. When the x-ray radiation penetrates through the material of the object, the lower-energy photons are filtered out to a greater or lesser extent, leading to material and path length-dependent beam hardening. The beam hardening leads to the photons at higher energy levels dominating the spectrum. By correcting the beam hardening, it is possible to obtain an accurate correction of the spectral variations of the x-ray source.

A feasible embodiment of a spectrally resolving radiation monitor is based on a direct conversion detector (quantum counting detector), which can distinguish between a plurality of energy ranges.

A further aspect can be the use of a detector described in the patent application WO2008/059425. The latter includes a sensitive layer which can convert photons into an electrical signal for measuring said photons.

A multi-layer detector is also feasible, wherein the spectral sensitivity is realized with the aid of the various layers.

These embodiments are expedient if the x-ray detector of the CT system is also based on the same technology. Then, the same energy thresholds for a subdivision into the various energy ranges can, in particular, be set at the detector and at the radiation monitor.

The invention claimed is:

1. A method for determining an attenuation of x-ray radiation as a result of the x-ray radiation penetrating through an object to be examined, the method comprising:
    receiving a signal of x-ray radiation intensity at a computer, the computer including a processor and a memory, wherein the processor
    establishes an intensity of the x-ray radiation, respectively before and after penetrating the object;

determines the spectral composition of the x-ray radiation prior to the x-ray radiation penetrating the object, said spectral composition being taken into account when determining the attenuation;

calculates a ratio, between the intensity of the x-ray radiation established after the penetration and the intensity of the x-ray radiation established prior to the penetration, for the respectively same energy range;

determines the attenuation using the calculated ratio and the determined spectral composition in the determination of the attenuation; and reconstructs an image corrected for inaccuarcies due at least to time variation of the determined x-ray spectrum based on the determined attenuation.

2. The method of claim 1, wherein the spectral composition of the x-ray radiation is determined by a radiation monitor.

3. The method of claim 1, wherein the processor back calculates the spectral composition using at least two energy ranges.

4. The method of claim 1, wherein the processor determines a further spectral composition of the x-ray radiation after penetrating through the object, wherein a comparison with the corresponding portions of the spectral composition of the x-ray radiation, determined prior to the penetration, is included in the determination of the attenuation.

5. The method of claim 1, wherein an accelerating voltage for generating the x-ray radiation is measured at time intervals within a period of time and the spectral composition of the x-ray radiation prior to the penetration through the object is derived from the accelerating voltage.

6. The method of claim 2, wherein the processor back calculates the spectral composition using at least two energy ranges.

7. A device, comprising:

a device configured to establish an intensity of x-ray radiation from an x-ray source and to determine a spectral composition of the x-ray radiation prior to penetration of the x-ray radiation through an object to be examined and configured to provide the established intensity and determined spectral composition to determine an attenuation of the x-ray radiation after the penetration of the x-ray radiation through the object be examined, wherein the device is arranged directly next to a shutter opening of a shutter of the x-ray source or integrated into the at least one x-ray source.

8. The device of claim 7, wherein the device is embodied as a radiation monitor for an x-ray machine.

9. The device of claim 7, wherein the device to accepts the established intensity and the determined spectral composition; and determines the attenuation of the x-ray radiation after the penetration of the x-ray radiation through the object, wherein the established intensity and the spectral composition of the x-ray radiation are usable for determining the attenuation.

10. The device of claim 7, further comprising:

at least two radiation monitor elements, wherein the radiation monitor elements have a different spectral sensitivity in respect of the spectral composition, acquirable thereby, of the x-ray radiation.

11. The device of claim 10, wherein, in terms of the longitudinal alignment thereof, the radiation monitor elements are arranged perpendicular to one another and perpendicular to the direction of the x-ray radiation to be received.

12. The device of claim 10, wherein a filter element is applied to at least one of the radiation monitor elements in such a way that the radiation monitor elements respectively have a different spectral sensitivity.

13. The device of claim 10, wherein the radiation monitor elements include different converter materials.

14. The device of claim 13, wherein the converter materials have different dimensions.

15. The device of claim 7, wherein the device is embodied in the form of a detector which includes a sensitive layer for converting photons into an electrical signal.

16. The device of claim 7, wherein the device is embodied in the form of a direct-conversion detector.

17. The device of claim 7, wherein the device is embodied in the form of a multi-layer detector.

18. An x-ray machine, comprising:

at least one x-ray source; and at least one x-ray detector for the imaging examination of an object arranged between x-ray source and x-ray detector, including the device of claim 8.

19. The x-ray machine of claim 18, wherein the radiation monitor is arranged directly next to a shutter opening of a shutter of the at least one x-ray source or integrated into the at least one x-ray source.

20. The x-ray machine of claim 18, wherein the device is configured to accept the established intensity and the determined spectral composition and the device is configured to determine the attenuation of the x-ray radiation after the penetration of the x-ray radiation through the object are integrated into the at least one x-ray detector.

21. An x-ray machine comprising the device of claim 7, wherein the device is embodied as a radiation monitor.

22. The device of claim 8, wherein the device accepts the established intensity and the determined spectral composition and determines the attenuation of the x-ray radiation after the penetration of the x-ray radiation through the object, wherein the established intensity and the spectral composition of the x-ray radiation are usable for determining the attenuation.

23. The device of claim 11, wherein a filter element is applied to at least one of the radiation monitor elements in such a way that the radiation monitor elements respectively have a different spectral sensitivity.

24. The device of claim 11, wherein the radiation monitor elements include different converter materials.

25. The x-ray machine of claim 18, wherein the x-ray machine is a CT system.

26. The x-ray machine of claim 19, wherein the device to accept the established intensity and the determined spectral composition and the device to determine the attenuation of the x-ray radiation after the penetration of the x-ray radiation through the object are integrated into the at least one x-ray detector.

* * * * *